United States Patent
Carceller et al.

(10) Patent No.: US 6,809,087 B2
(45) Date of Patent: Oct. 26, 2004

(54) SODIUM SALT OF AN AZO DERIVATIVE OF 5-AMINOSALICYLIC ACID

(76) Inventors: Elena Carceller, Barcelona (ES); Jorge Salas Solana, Barcelona (ES); José Ignacio Escamilla, Barcelona (ES); Joaquim Ramis, Barcelona (ES); Javier Forn, Barcelona (ES)

(*) Notice: Subject to any disclaimer, the term of this patent is extended or adjusted under 35 U.S.C. 154(b) by 63 days.

(21) Appl. No.: 10/257,262

(22) PCT Filed: Apr. 10, 2001

(86) PCT No.: PCT/EP01/04109
§ 371 (c)(1),
(2), (4) Date: May 6, 2003

(87) PCT Pub. No.: WO01/77109
PCT Pub. Date: Oct. 18, 2001

(65) Prior Publication Data
US 2003/0176401 A1 Sep. 18, 2003

(30) Foreign Application Priority Data
Apr. 10, 2000 (ES) .......................................... 2000-00996

(51) Int. Cl.⁷ ..................... A61K 31/655; C07D 471/04
(52) U.S. Cl. .................... 514/150; 534/588; 534/664
(58) Field of Search ................................ 534/588, 664; 514/150

(56) References Cited

U.S. PATENT DOCUMENTS

| 4,312,806 A | | 1/1982 | Lambert et al. | |
|---|---|---|---|---|
| 5,747,477 A | * | 5/1998 | Carceller et al. | ........... 514/150 |

FOREIGN PATENT DOCUMENTS

| WO | 92 03423 | 3/1992 |
|---|---|---|
| WO | 96 14317 | 5/1996 |
| WO | 97 09329 | 3/1997 |

* cited by examiner

*Primary Examiner*—Fiona T. Powers

(57) ABSTRACT

The present invention relates to the sodium salt of (Z)-2-hydroxy-5-([4-[3-[4-[(2-methyl-1H-imidazo[4,5-c]pyridin-1-yl)methyl ]-1-piperidinyl]-3-oxo-1-phenyl-1-propenyl] phenyl]azo]benzoic acid, as well as to the pharmaceutical compositions containing it, to a procedure for its preparation and to its use for the manufacture of medicaments for the treatment or prevention of inflammatory bowel disease.

54 Claims, 8 Drawing Sheets

SODIUM SALT OF AN AZO DERIVATIVE OF 5-AMINOSALICYLIC ACID

FIELD OF THE INVENTION

The present invention relates to a new salt of an azo derivative of 5-aminosalicylic acid, and more particularly to the sodium salt of (Z)-2-hydroxy-5-[[4-[3-[4-[(2-methyl-1H-imidazo[4,5-c ]pyridin-1-yl)methyl]-1-piperidinyl]-3-oxo-1-phenyl-1-propenyl]phenyl]azo]benzoic acid. The present invention also relates to the pharmaceutical compositions containing it, to a procedure for its preparation and to its use for the manufacture of medicaments useful for the treatment or prevention of inflammatory bowel disease.

BACKGROUND OF THE INVENTION

Inflammatory bowel disease is a chronic inflammatory disease of the intestine, whose etiology is still unknown. The most prevalent forms of this disease are ulcerative colitis and Crohn's disease.

Patent application WO 97/09329 discloses a series of azo derivatives of 5- aminosalicylic acid (5-ASA) that are useful for the treatment of inflammatory bowel disease. These compounds combine in the same molecule 5-ASA and a compound having PAF-antagonist activity through an azo bond, and are designed to be metabolized in the colon by the intestinal bacteria in a similar manner to that described for the reference compound sulfasalazine, to deliver 5-ASA and the PAF antagonist. One of the compounds described in this patent application is (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid, which is known in the literature as UR-12746 and whose formula is shown below:

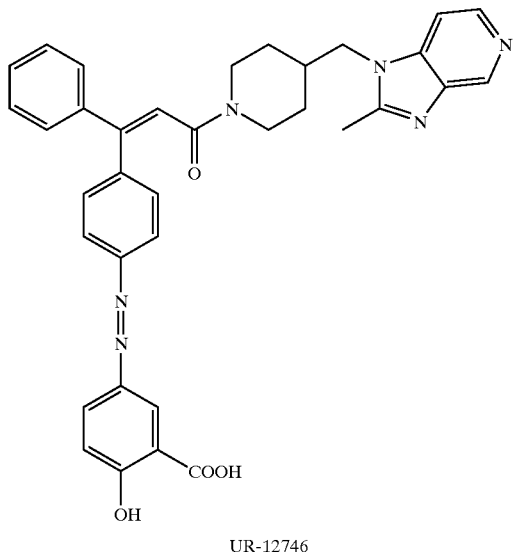

UR-12746

The authors of the present invention have found that the levels of azoreduction observed with this compound are low when studies on the metabolization of said azo bond are carried out. Since this kind of compounds are precisely designed to be metabolized and deliver in the colon 5ASA and the PAF antagonist, which are the active molecules, the problem arises of finding compounds that are metabolized in the colon to a greater extent. This problem is solved with the new salt that is the object of the present invention.

SUMMARY OF THE INVENTION

The present invention relates to the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid of formula I:

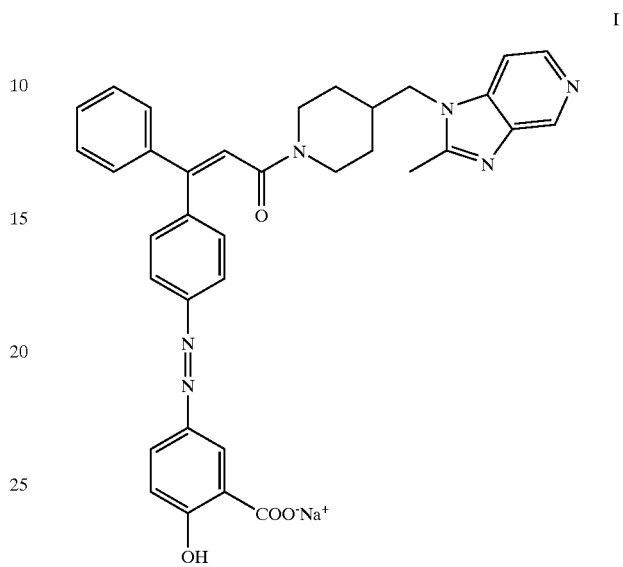

I

It has been found that the sodium salt of the invention (i.e. the sodium salt of UR-12746) can exist in different forms, in particular in amorphous or noncrystalline form and in crystalline form. It has further been found that the sodium salt of the invention exists in two different crystalline forms, designated polymorph I and polymorph II, depending on the preparation conditions, as explained in greater detail below. The present invention relates to the sodium salt of UR-12746 in any of its forms.

The present invention also relates to a process for the preparation of the sodium salt of formula I.

The present invention further relates to a pharmaceutical composition which comprises an effective amount of the sodium salt of formula I and one or more pharmaceutically acceptable excipients.

The present invention also relates to the use of the sodium salt of formula I for the manufacture of a medicament for the treatment or prevention of inflammatory bowel disease. Throughout the present description, the term "inflammatory bowel disease" is to be understood as comprising ulcerative colitis, Crohn's disease as well as any other form of inflammatory bowel disease.

pyridin-1-yl)methyl]-1-piperidinyl]-3-oxo-1-phenyl-1-propenyl]-phenyl]azo]benzoic acid.

Figure 4:
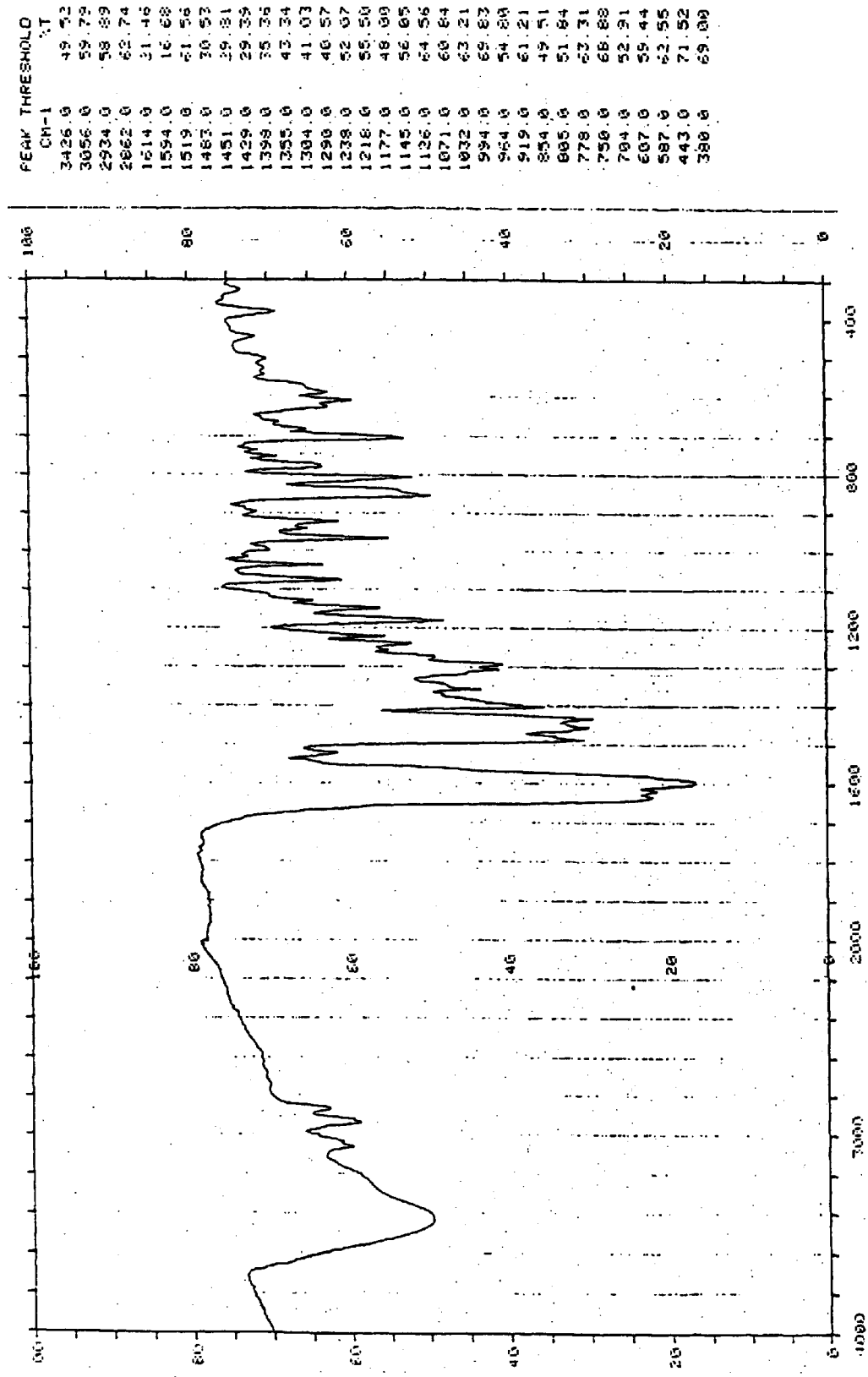

FIG. 4 shows a representative infrared spectrum of polymorph I of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid.

Figure 5:
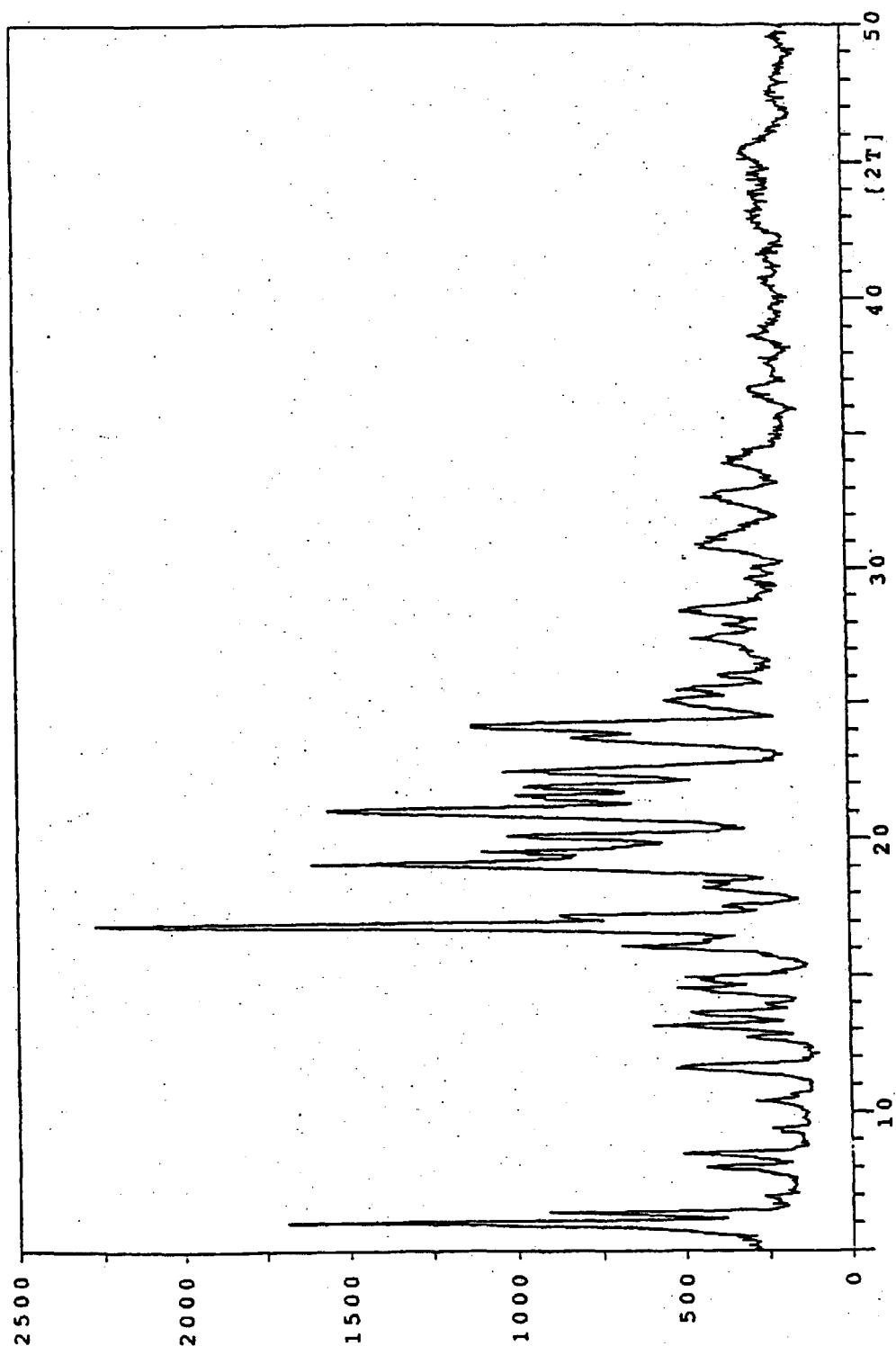

FIG. 5 shows a representative X-ray powder diffractogram of polymorph I of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azolbenzoic acid.

Figure 6:
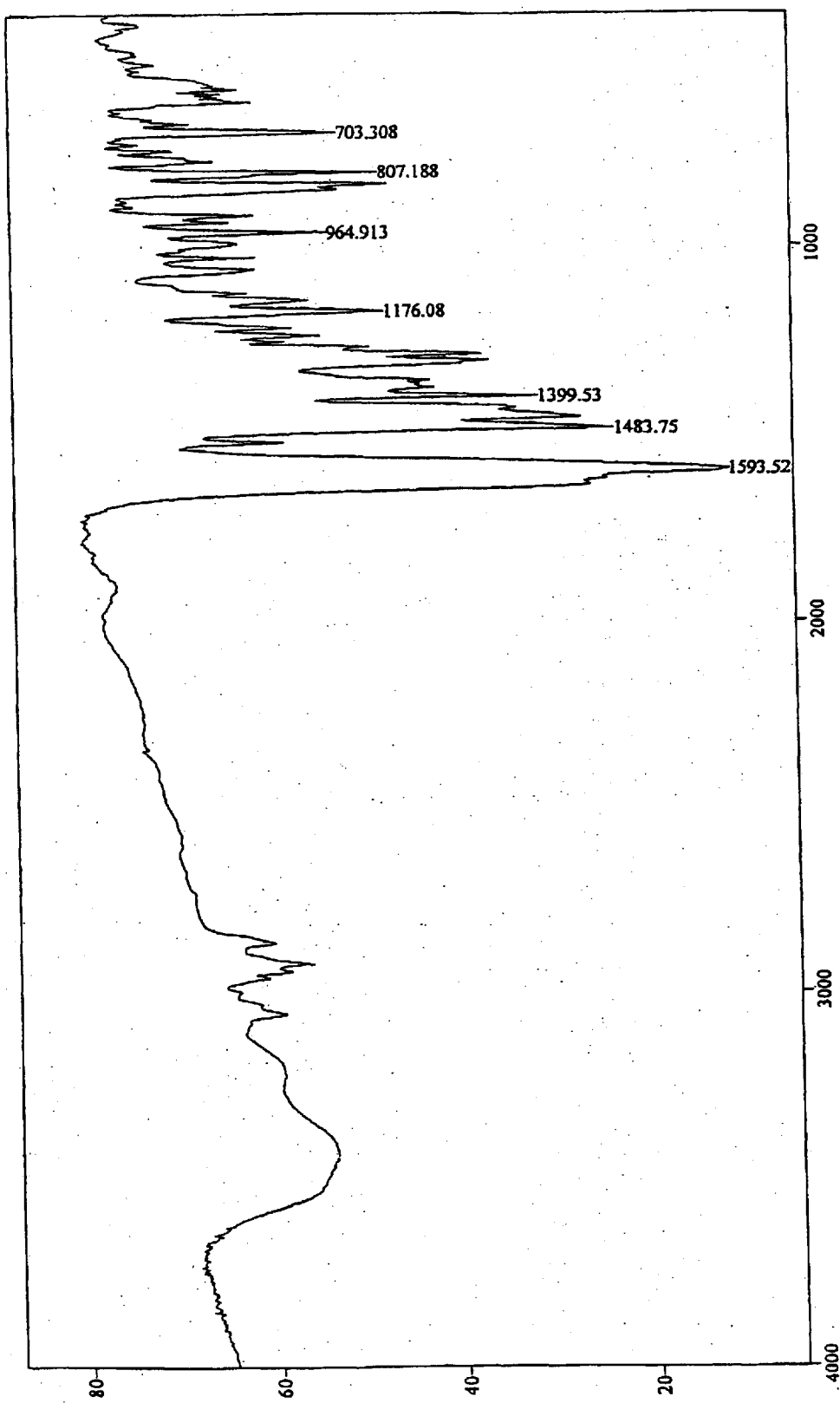

FIG. 6 shows a representative infrared spectrum of polymorph II of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid.

Figure 7:
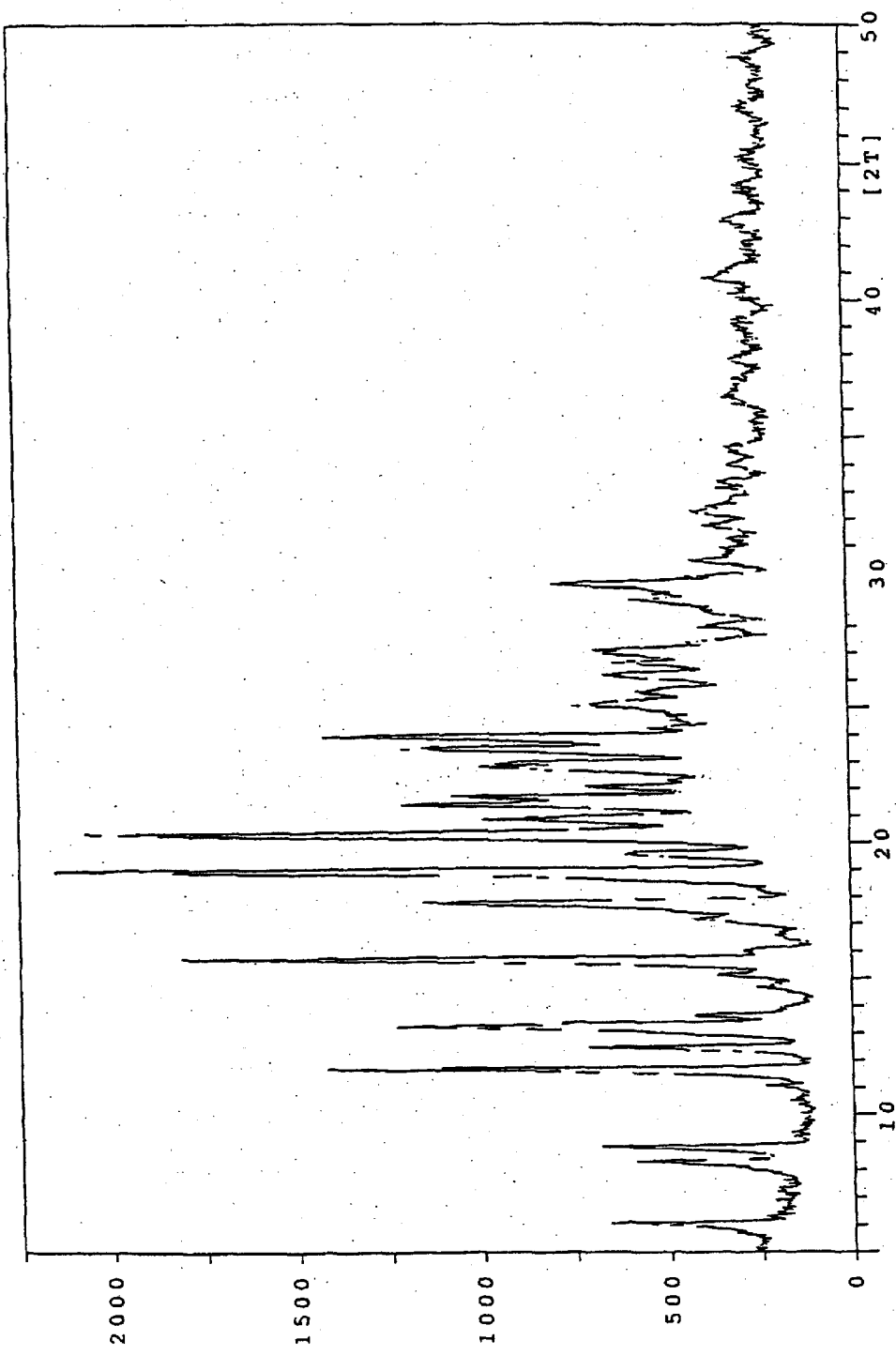

FIG. 7 shows a representative X-ray powder diffractogram of polymorph II of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid.

Figure 8:
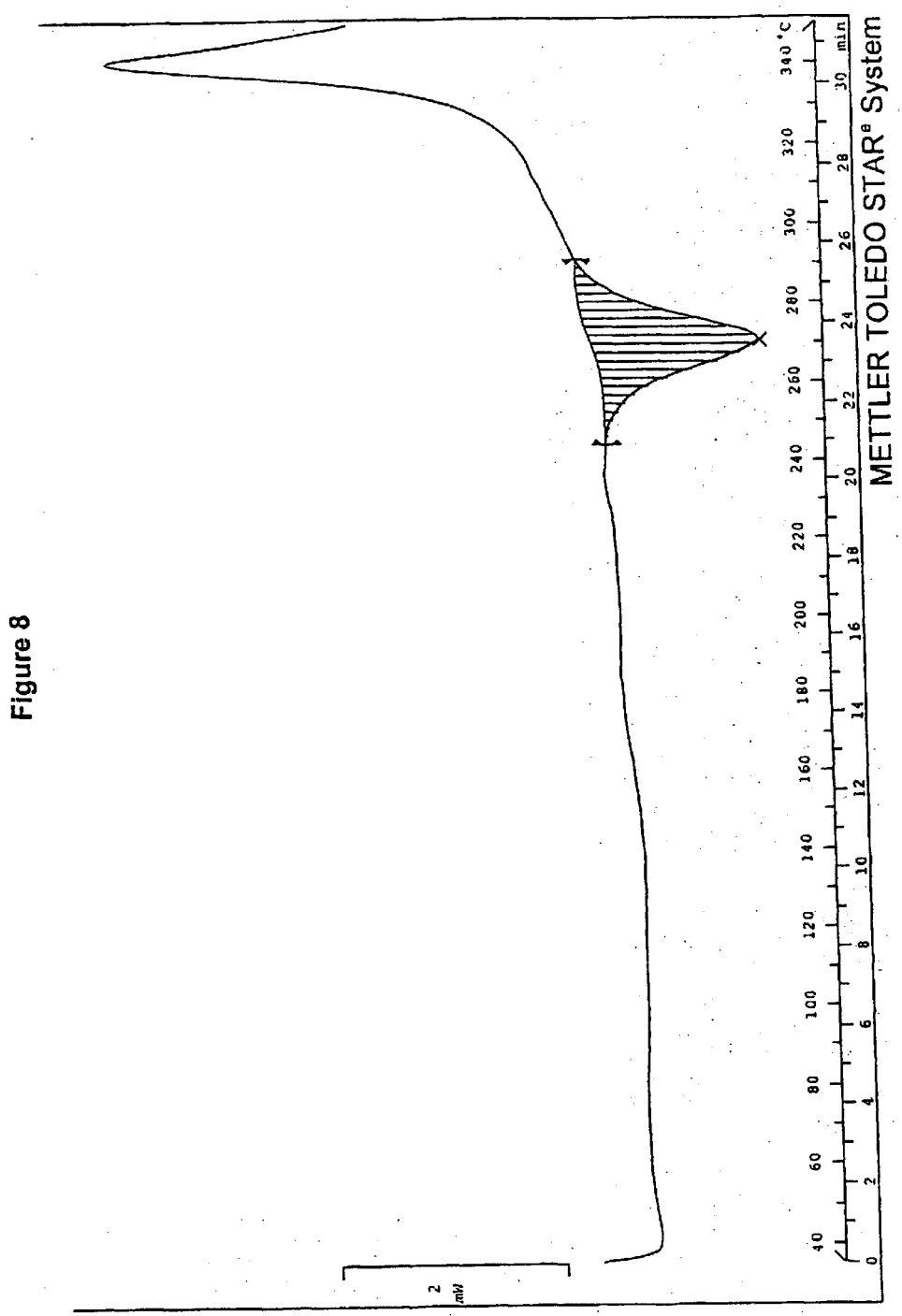

FIG. 8 shows a representative differential scanning calorimetry (DSC) diagram of polymorph II of the sodium salt of (Z)-2-hydroxy-5-[[4-[3-[4-[(2-methyl-1H-imidazo [4,5-c]pyridin-1-yl)methyl]-1-piperidinyl]-3-oxo-1-phenyl-1-propenyl]-phenyl]azo]benzoic acid.

DESCRIPTION OF THE INVENTION

As mentioned above, the present invention relates to the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid, of formula I:

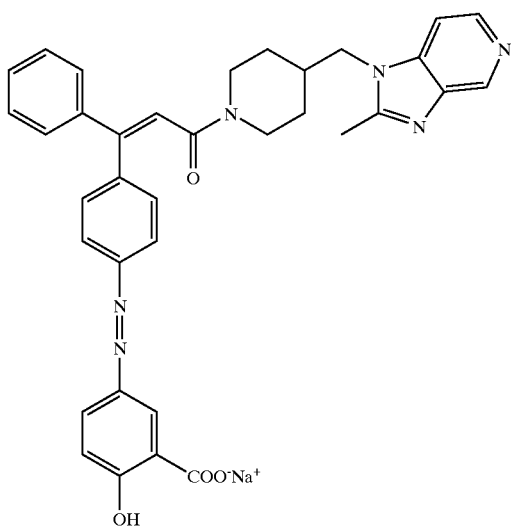

I

Throughout the present description, we will refer to the new sodium salt that is the object of the invention as the sodium salt of (Z)-2-hydroxy-5-[[4-[3-(4-[(2-methyl-1H-imidazo[4,5-c]pyridin-1-yl)methyl]-1-piperidinyl]-3-oxo-1-phenyl-1-propenyl]phenyl]azo]benzoic acid, the sodium salt of formula I or the sodium salt of UR-12746, without distinction.

Surprisingly, the authors of the present invention have found that the sodium salt of formula I is metabolized in the colon to a much greater extent than the corresponding acid compound described in the prior art, that is UR-12746. Therefore, the new salt that is the object of the invention is a more suitable compound for the manufacture of medicaments for the treatment or prevention of inflammatory bowel disease.

As mentioned above, it has been found that the sodium salt of the invention can exist in amorphous or non-crystalline form and in crystalline form, depending on the conditions under which it is obtained, as described in more detail below. The present invention relates to the sodium salt of UR-12746 in any of its forms.

In an embodiment of the invention, the sodium salt of formula I is provided in amorphous form.

In another embodiment of the invention, the sodium salt of formula I is provided in crystalline form.

In another embodiment, the invention provides the polymorph I of the sodium salt of formula I, which exhibits an X-ray powder diffractogram, obtained at $\lambda=1.542$ Å and using a radiation source of Cu K$\alpha$, comprising peaks at an angle 2$\theta$ of 6.04, 6.38, 8.01, 8.54, 11.73, 13.18, 13.65, 14.55, 14.97, 16.08, 16.90, 17.23, 19.10, 19.53, 20.15, 21.12, 21.86, 22.48, 23.71 and 24.23°±0.2°.

In another embodiment, the polymorph I of the sodium salt of formula I has an X-ray powder diffractogram substantially in accordance with that shown in FIG. 5.

In another embodiment, the polymorph I of the sodium salt of formula I has an infrared spectrum substantially in accordance with that shown in FIG. 4.

In another embodiment, the polymorph I of the sodium salt of formula I has an X-ray powder diffractogram substantially in accordance with that shown in FIG. 5 and an infrared spectrum substantially in accordance with that shown in FIG. 4.

In another embodiment, the invention provides polymorph II of the sodium salt of formula I, which exhibits an X-ray powder diffractogram, obtained at $\lambda=1.542$ Å and using a radiation source of Cu K$\alpha$, comprising peaks at an angle 2$\theta$ of 6.07, 8.30, 8.82, 11.71, 12.52, 13.24, 15.72, 17.77, 18.96, 19.67, 20.33, 20.84, 21.39, 21.71, 22.77, 22.97, 23.50, 23.95 and 29.50°±0.2°.

In another embodiment, the polymorph II of the sodium salt of formula I has an X-ray powder diffractogram substantially in accordance with that shown in FIG. 7.

In another embodiment, the polymorph II of the sodium salt of formula I has an infrared spectrum substantially in accordance with that shown in FIG. 6.

In another embodiment, the polymorph II of the sodium salt of formula I has an X-ray powder diffractogram substantially in accordance with that shown in FIG. 7 and an infrared spectrum substantially in accordance with that shown in FIG. 6.

The present invention further provides a pharmaceutical composition which comprises the sodium salt of formula I in any of its forms and one or more pharmaceutically acceptable excipients. In a preferred embodiment, the pharmaceutical composition is adapted for oral administration.

The present invention further provides the use of the sodium salt of formula I in any of its forms for the manufacture of a medicament for the treatment or prevention of inflammatory bowel disease, including ulcerative colitis and Crohn's disease.

The present invention also relates to the use of the sodium salt of formula I in any of its forms for the treatment or prevention of inflammatory bowel disease, including ulcerative colitis and Crohn's disease.

The present invention further relates to the sodium salt of formula I in any of its forms for use in therapy, and particularly for the treatment or prevention of inflammatory bowel disease, including ulcerative colitis and Crohn's disease.

The present invention further relates to a method of treating or preventing inflammatory bowel disease, including ulcerative colitis and Crohn's disease, in a mammal in need thereof, specially a human being, which comprises administering to said mammal a therapeutically effective amount of the sodium salt of formula I in any of its forms.

The sodium salt of formula I can be obtained by any conventional procedure for preparing salts. For example, it can be prepared from (Z)-2-hydroxy-5-[[4-[3-[4-[(2-methyl-1H-imidazo [4,5-c]pyridin-1-yl)methyl]-1-piperidinyl]-3-oxo-1-phenyl-1-propenyl]phenyl]azo]benzoic acid by treatment with one equivalent of sodium hydroxide in a suitable solvent. As examples of suitable solvents we can mention ethanol and methanol.

The sodium salt of formula I is obtained as an amorphous solid from a solution of said sodium salt of UR-12746, either by evaporation of the solvent or by precipitation, for example by the addition over a second more apolar solvent, as explained in more detail in example 1.

The sodium salt of formula I is obtained in crystalline form by crystallization of a solution of the sodium salt of UR-12746 in a suitable solvent or solvents. Depending on the conditions under which the crystallization is carried out, the sodium salt of formula I is obtained as polymorph I or polymorph II.

The source solution of sodium salt of UR-12746 to carry out the crystallization can be obtained either by treatment of UR-12746 with sodium hydroxide, as mentioned above, or can be prepared from sodium salt of UR-12746 previously obtained.

To obtain polymorph 1, crystallization is preferably carried out using ethanol as the solvent. We have found that the product crystallizes well from a solution in ethanol at a crystallization temperature in the range 20–70° C. Preferably, the solution contains a concentration of sodium salt of UR-12746 (expressed as mL solvent/g of UR-12746 used as starting material) in the range 1.9–6.0 mL/g and must contain the lowest possible amount of water, in any case below 4% w/w. The preparation of polymorph I of the sodium salt of UR-12746 is explained in greater detail in example 2.

Polymorph II is preferably obtained from mixtures of ethanol or methanol with a second more apolar solvent such as ethyl acetate, acetonitrile or heptane and optionally in the presence of a small amount of water. For example, we have found that polymorph II crystallizes well in a mixture of ethanol-ethyl acetate- water. Preferably, the solution contains a concentration of sodium salt of UR- 12746 (given as mL solvent/g starting material (i.e. UR-12746 or UR-12746 sodium salt) expressed as g UR-12746) of 2.8–6.6 mL ethanol/g, 5.4–15 mL ethyl acetate/g and 0.13–0.33 mL water/g and crystallization is carried out at a temperature in the range between 25 and 70° C. The preparation of polymorph II of the sodium salt of UR-12746 is explained in greater detail in examples 3 and 4.

As will be obvious to those skilled in the art, crystallization can be stimulated, if desired, by seeding the solution with pure previously-obtained seed crystals of the crystalline form that it is desired to obtain.

Polymorph I and polymorph II exhibit significantly different X-ray powder diffractograms and infrared spectra and thus can be distinguished using any of these two techniques. X-ray powder diffractograms representative of polymorph I and polymorph II are shown in FIGS. 5 and 7, respectively, whereas representative infrared spectra are shown in FIGS. 4 and 6.

The region of the X-ray powder diffractograms that is more useful to distinguish polymorph I and polymorph II is the region occurring between 16.5° and 18° (angle 2θ). Polymorph I exhibits a strong peak at 16.90°, not present in polymorph II, whereas the latter exhibits a strong peak at 17.77°, not present in polymorph I.

In case infrared spectroscopy is used to distinguish the two polymorphs, the regions of the spectra that are more useful to distinguish the two polymorphs are between 800 and 900 cm$^{-1}$ and between 550 and 650 cm$^{-1}$.

DSC, on the contrary, is not a suitable method to distinguish the two polymorphs because they exhibit very similar melting points.

As will be obvious to those skilled in the art, the values of the angle 2θ in the X-ray powder diffractograms as well as the relative intensity of the peaks may vary depending on the particular instrument used as well as on the preparation of the sample. For this reason, the 2θ values mentioned to describe polymorphs I and II should not be considered as absolute values but may vary by ±0.2°.

The sodium salt of UR-12746 that is the object of the present invention is useful, as mentioned above, for the treatment or prevention of inflammatory bowel disease in mammals, including man. The compound of the present invention is preferably administered orally, although it can also be adapted to other modes of administration, particularly rectal administration.

The present invention also relates to the pharmaceutical compositions which comprise the compound of the present invention and one or more excipients or other auxiliary agents if necessary. Said compositions can be analogous to those described for UR-12746 in patent application WO 97/09329, which is herein incorporated as reference, and can be prepared following standard pharmaceutical formulation techniques.

Solid compositions for oral administration include tablets, dispersible powders, granules and capsules. In tablets, the active component is admixed with at least one inert diluent such as lactose, starch, mannitol or calcium phosphate; binding agents for example corn starch, gelatine, microcrystalline cellulose or polyvinylpyrrolidone; and lubricating agents for example magnesium stearate, stearic acid or talc. The tablets may be coated according to methods well known in normal pharmaceutical practice. Formulations for oral use also include capsules of absorbable material, such as gelatin, containing the active ingredient with or without the addition of inert solid diluents or other excipients.

Oral compositions may also be presented as dispersible powders and granules suitable for the preparation of a suspension by the addition of water or other suitable vehicle. These preparations comprise the active ingredient and excipients such as dispersing or wetting agents, suspending agents, such as sodium carboxymethylcellulose, methylcellulose, hydroxypropylmethylcellulose, sodium alginate, polyvinylpyrrolidone, gum tragacanth, xantham gum, gum acacia, and preservatives, such as methyl or propyl p-hydroxybenzoate. Additional excipients, for example sweetening, flavouring and colouring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise conventional additives such as wetting agents, suspending agents, sweetening, flavouring, preserving agents and buffers.

The compound of the invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides.

The dosage and frequency of dose may vary depending upon several factors including symptoms, age and body weight of the patient. In general, the compound of the invention may be administered orally or rectally to human patients at a daily dosage of from about 500 to about 10000 mg for an adult, which may be administered either as a single dose or as divided doses. However, in special cases and at the discretion of the attending physician, doses outside this margin may be required.

The following examples illustrate, but do not limit, the scope of the present invention. Instruments that have been used:
- infrared spectra were recorded in KBr discs using a spectrophotometer Perkin Elmer 983 (examples 1 and 2) or Bomen MB-100 (example 3);
- DSC spectra were recorded using a Mettler TA-3000 apparatus and a DSC-20 coupled to a computer system equipped with the Mettler Toledo STAR$^e$ System software;
- X-ray powder diffractograms were recorded by means of a Philips Xpert-MPD automated powder diffractometer and using a radiation source of Cu Kα(λ=1.542 Å).

EXAMPLE 1

Preparation of the sodium salt of (Z)-2-hydroxy-5-[[4-[3-[4-[(2-methyl-1H-imidazo [4,5-c]pyridin-1-yl)methyl]-1-piperidinyl]-3-oxo-1-phenyl-1-propenyl]phenyl]azo]benzoic acid in amorphous form 107 mg of NaOH was dissolved in 67 mL of boiling methanol. 1.7 g of (Z)-2-hydroxy-5-[[4-[3-[4-[(2-methyl-1H-imidazo[4,5-c]pyridin-1-yl)methyl]-1-piperidi-nyl]-3-oxo-1-phenyl-1-propenyl]phenyl]azo]benzoic acid (obtained according to the method described in patent application WO 97/09329) was added, and the mixture was further heated for 10 min. The mixture was filtered while still hot, concentrated to a volume of 5 mL and the resulting solution was added dropwise to ethyl acetate (30 mL) at room temperature and under stirring, to yield a fine yellow solid. This solid was filtered and dried in vacuo at 70° C., to give 1.5 g of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid in amorphous form.

Figure 1:
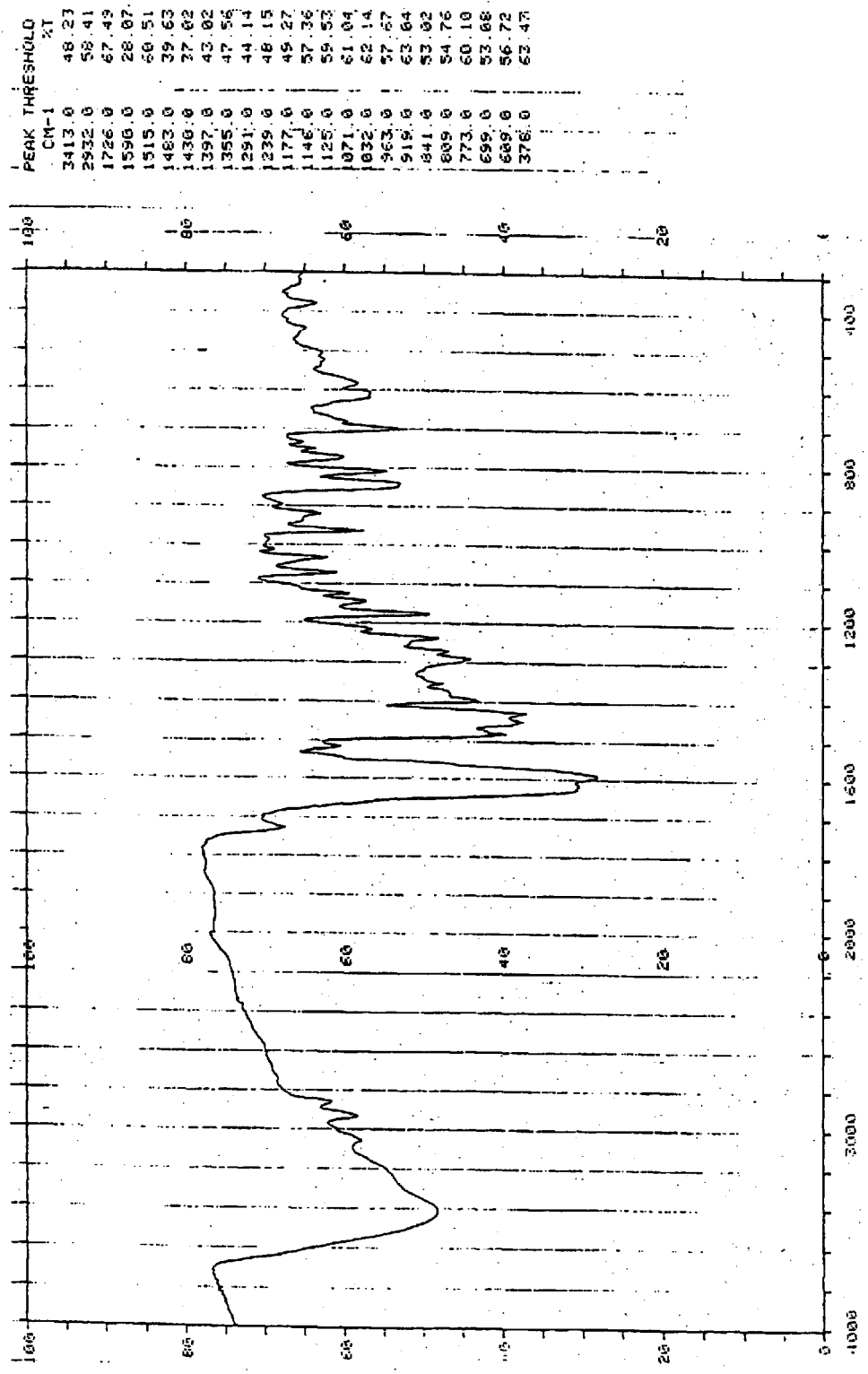
FIG. 1 shows a representative infrared spectrum of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid in amorphous form.
Figure 2:
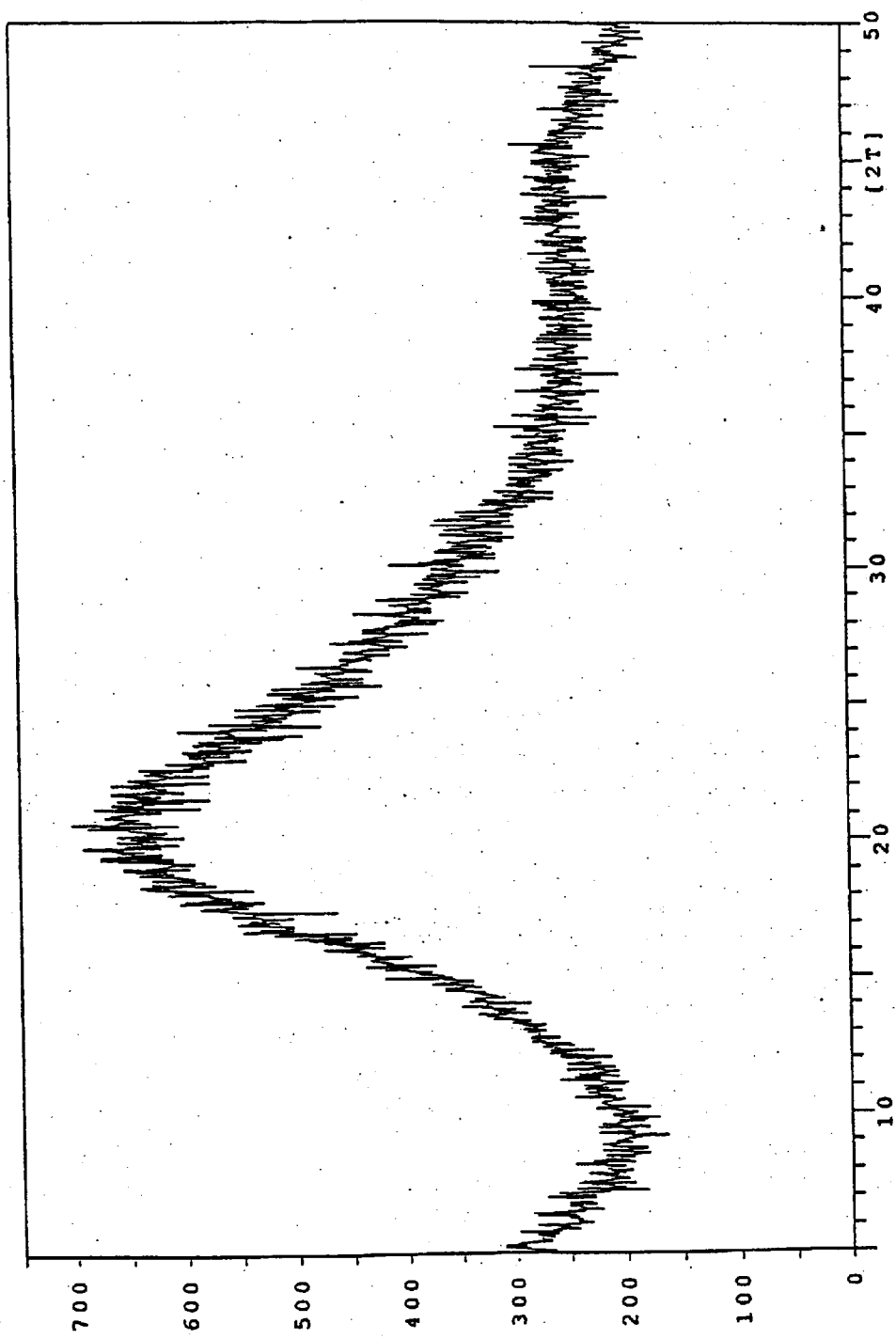
FIG. 2 shows a representative X-ray powder diffractogram of the sodium salt of (Z)-2-hydroxy-5-[[4-[3-[4-[(2-methyl-1H-imidazo[4,5-c]pyridin-1-yl)methyl ]-1-piperidinyl]-3-oxo-1-phenyl-1-propenyl]phenyl]azo] benzoic acid in amorphous form.

The product obtained exhibits a flat DSC diagram that is characteristic of amorphous products, with a small heat absorption at about 260° C. A representative infrared spectrum of this product is shown in FIG. 1. By means of X-ray powder diffraction, the compound was shown to be amorphous; its corresponding diffractogram is shown in FIG. 2.

EXAMPLE 2

Preparation of polymorph I of the sodium salt of (Z)-2-hydroxy-5-[[4-[3-[4-[(2-methyl-1H-imidazo[4,5-c]pyridin-1-yl)methyl]-1-piperidinyl-3-oxo-1-phenyl-1-propenyl]phenyl]azo]benzoic acid To a suspension of 100.0 g of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]-phenyl]azo] benzoic acid (93.3% assay) in 1.5 L of absolute ethanol, 6.58 g of sodium hydroxide was added and the mixture was stirred at 60–65° C. till dissolution. The resulting solution was filtered and concentrated by distillation in vacuo to a volume of 200–300 mL. This concentrated solution was stirred at 55–65° C. for about 4 hours, giving rise to an abundant precipitate. Heating was stopped and the mixture was further stirred at room temperature (18–22° C.) for about 16–20 hours. The product was centrifuged, washed in the centrifuge with absolute ethanol (2×10 mL) and dried in vacuo at 80° C. 85–87 g of the polymorph I of the sodium salt of (Z)-2-hydroxy-5-[[4-[3-[4-[(2-methyl-1H-imidazo [4,5-c]pyridin-1-il)methyl]-1-piperidinyl]-3-oxo-1-phenyl-1-propenyl]phenyl]azo]benzoic acid was obtained.

Figure 3:
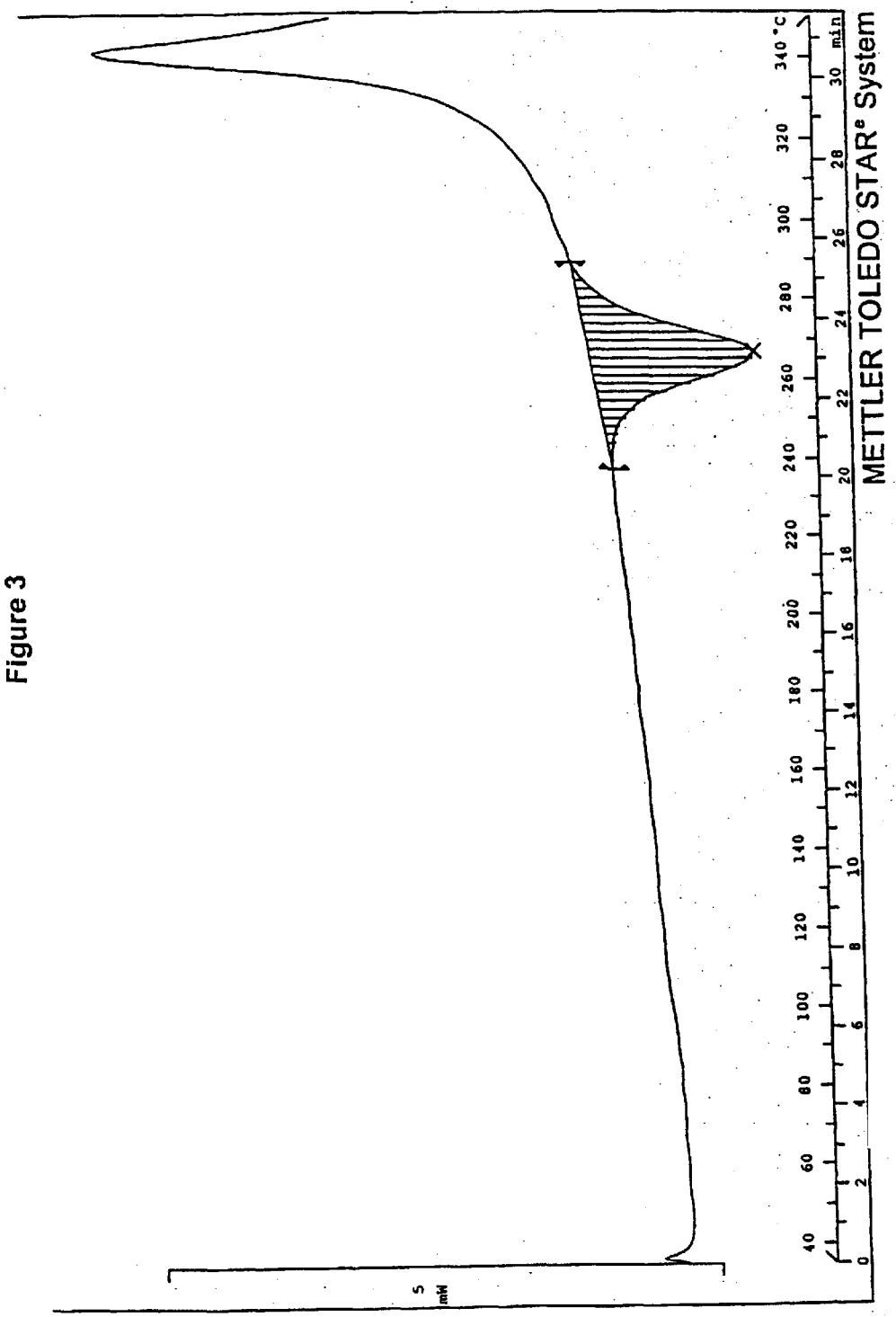
FIG. 3 shows a representative differential scanning calorimetry (DSC) diagram of polymorph I of the sodium salt of (Z)-2-hydroxy-5-[[4-[3-[4-[(2-methyl-1H-imidazo [4,5-c]

A representative DSC diagram of polymorph I is shown in FIG. 3. The product exhibits a DSC melting peak usually in the range 263–267° C. A representative infrared spectrum of polymorph I is shown in FIG. 4. A representative X-ray powder diffractogram of polymorph I is shown in FIG. 5. The values of angle 2θ (in degrees), spacing "d" (in Angstroms) and relative intensity (%) of said X-ray diffractogram are shown in Table 1 in numerical form for the peaks having a relative intensity equal or higher than 10%.

TABLE 1

| Angle 2θ (°) | d (Å) | Relat. Int. (%) |
|---|---|---|
| 6.035 | 14.645 | 74 |
| 6.375 | 13.865 | 36 |
| 8.010 | 11.038 | 15 |
| 8.535 | 10.360 | 18 |
| 11.725 | 7.548 | 16 |
| 13.180 | 6.718 | 22 |
| 13.650 | 6.487 | 17 |
| 14.545 | 6.090 | 19 |
| 14.970 | 5.918 | 15 |
| 16.080 | 5.512 | 26 |
| 16.895 | 5.248 | 100 |
| 17.225 | 5.148 | 35 |
| 17.580 | 5.045 | 11 |
| 18.200 | 4.874 | 14 |
| 18.445 | 4.810 | 15 |
| 19.095 | 4.648 | 71 |
| 19.530 | 4.545 | 46 |
| 20.145 | 4.408 | 39 |
| 21.115 | 4.208 | 61 |
| 21.430 | 4.146 | 37 |
| 21.565 | 4.121 | 41 |
| 21.855 | 4.067 | 40 |
| 22.480 | 3.955 | 40 |
| 23.710 | 3.753 | 32 |
| 24.060 | 3.699 | 44 |
| 24.230 | 3.673 | 41 |
| 25.140 | 3.542 | 18 |
| 25.535 | 3.488 | 17 |
| 26.065 | 3.419 | 12 |
| 27.400 | 3.255 | 16 |
| 27.905 | 3.197 | 10 |
| 28.330 | 3.150 | 16 |
| 30.815 | 2.902 | 14 |
| 32.880 | 2.724 | 11 |

EXAMPLE 3

Preparation of polymorph II of the sodium salt of (Z)-2-hydroxy-5-[[4-[3-4-[(2-methyl-1H-imidazo [4,5-c]pyridin1-yl)methyl]-1-piperidinyl]-3oxo-1-phenyl-1-propenyl]phenyl]azo]benzoic acid from polymorph I of the sodium salt of UR-12746

41 g of the polymorph I of the sodium salt of UR-12746 was dissolved in 160 mL of absolute ethanol and 11 mL of water, at 60–65° C. To this solution, 500 mL of ethyl acetate was added slowly, keeping the temperature at 65–70° C. The solution was cooled down to room temperature over 2 hours, whereby the product crystallized, and was further cooled in an ice bath for 2 more hours. The product was centrifuged and dried in vacuo at 80° C., yielding 30 g of polymorph II.

A representative DSC diagram of polymorph II is shown in FIG. 8. The product exhibits a DSC melting peak usually in the range 264–275° C. A representative infrared spectrum of polymorph II is shown in FIG. 6. A representative X-ray powder diffractogram of polymorph II is shown in FIG. 7.

The values of angle 2θ (in degrees), spacing "d"(in Angstroms) and relative intensity (%) of said X-ray diffractogram are shown in Table 2 in numerical form for the peaks having a relative intensity equal or higher than 10%.

TABLE 2

| Angle 2θ (°) | d (Å) | Relat. Int. (%) |
| --- | --- | --- |
| 6.065 | 14.573 | 27 |
| 8.295 | 10.659 | 23 |
| 8.820 | 10.026 | 28 |
| 11.710 | 7.557 | 63 |
| 12.520 | 7.070 | 29 |
| 13.235 | 6.690 | 55 |
| 13.400 | 6.608 | 34 |
| 13.695 | 6.466 | 15 |
| 15.155 | 5.846 | 11 |
| 15.715 | 5.639 | 86 |
| 17.165 | 5.166 | 15 |
| 17.770 | 4.991 | 51 |
| 18.955 | 4.682 | 100 |
| 19.670 | 4.513 | 23 |
| 20.330 | 4.368 | 92 |
| 20.835 | 4.264 | 43 |
| 21.390 | 4.154 | 54 |
| 21.710 | 4.094 | 46 |
| 22.080 | 4.026 | 29 |
| 22.770 | 3.905 | 41 |
| 22.965 | 3.873 | 39 |
| 23.495 | 3.787 | 50 |
| 23.950 | 3.716 | 59 |
| 24.270 | 3.667 | 19 |
| 25.060 | 3.553 | 31 |
| 25.605 | 3.479 | 21 |
| 26.230 | 3.398 | 24 |
| 26.640 | 3.346 | 25 |
| 27.135 | 3.286 | 27 |
| 27.960 | 3.191 | 13 |
| 28.495 | 3.132 | 12 |
| 28.960 | 3.083 | 23 |
| 29.500 | 3.028 | 31 |
| 29.895 | 2.989 | 13 |
| 30.480 | 2.933 | 14 |
| 31.725 | 2.821 | 12 |
| 32.220 | 2.778 | 13 |
| 33.400 | 2.683 | 11 |
| 40.720 | 2.216 | 11 |

EXAMPLE 4

Preparation of polymorph II of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid from UR-12746

14.80 g of UR-12746 and 0.96 g of sodium hydroxide was dissolved in 225 mL of ethanol containing 3.15% (w/w) of water. The mixture was heated at 45–50° C. until dissolution and was then filtered. The filtrate was concentrated in vacuo, distilling off about 180 mL of ethanol from the solution. To the concentrated solution 2 mL of water was added, and the resulting solution was heated at 65° C. At 60–65° C. 80 mL of ethyl acetate was added slowly and in portions. The resulting solution was cooled down to room temperature over 3 hours, whereby the product crystallized. The product obtained was centrifuged and dried in vacuo at 80° C., yielding 4.75 g of polymorph II.

EXAMPLE 5

Comparative study of the azoreduction of UR-12746 and the sodium salt of UR-12746 after oral administration As mentioned above, UR-12746 is a compound designed to be metabolized in the colon by the intestinal bacteria to deliver 5-ASA and an amine with PAF antagonist activity, UR-12715.

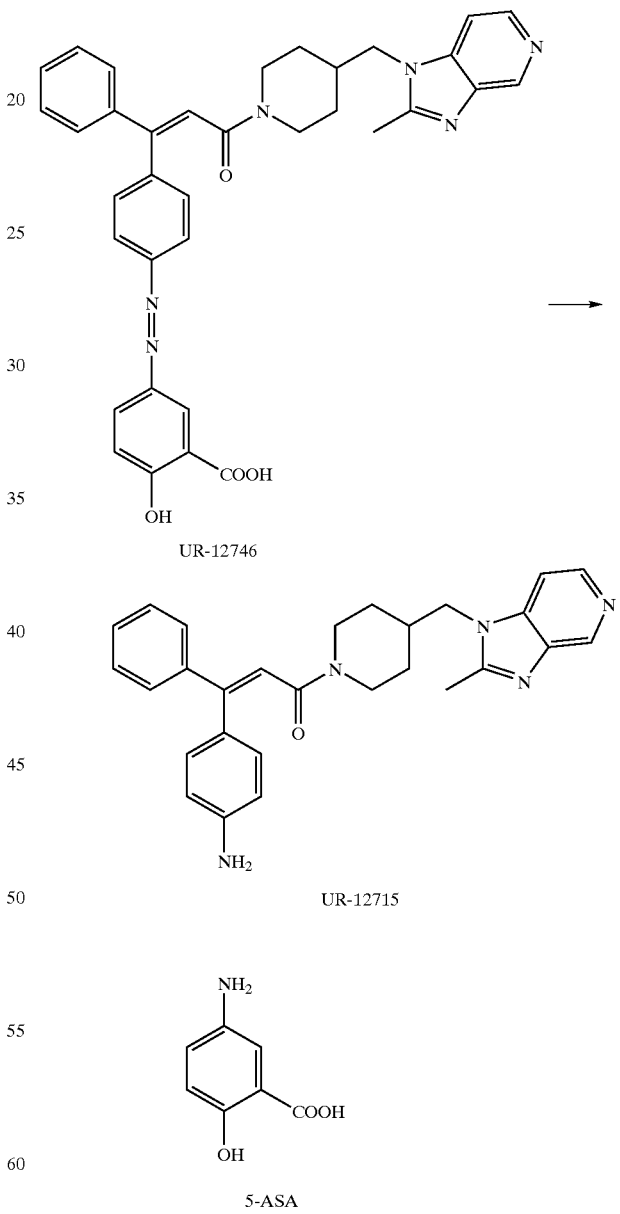

The level of azoreduction has been studied by determining the distribution of UR-12746 and UR-12715 in faeces after the oral administration of UR-12746 and its sodium salt in rats and monkeys.

i) Study in rats

For the study in rats, 6 female Sprague-Dawley rats weighing between 169 and 185 g were used. UR-12746 and the sodium salt of UR-12746 (polymorph I) were orally administered to three rats each as a suspension in 0.2% carboxymethylcelulose (CMC), at a dose of 50 mg/kg (100 mg of test compound/10 mL of 0.2% CMC).

The rats were placed in metabolic cages, so that urine and faeces could be separately collected, and faeces were collected during the periods 0–24 h and 24–48 h. The faeces collected in the same period were weighted and crumbled. Water was added (2 mL of water/g of faeces) and the paste obtained was stirred to homogeneity. The total weight of the homogenate was then determined.

An aliquot of this homogenate (about 2 g) was mixed with 4 mL of MeOH, stirred in a Vortex and centrifuged for 10 minutes at 4500 rpm (3000 g). The supernatant was filtered through a 0.45 μm filter, and the concentrations of the administered product and metabolite present in the sample were determined by a HPLC chromatographic method with gradient elution and ultraviolet detection, under the conditions detailed below:

| Column: | Hypersil—Elite C18 5 μm (4.6 x 150 mm) | | | |
|---|---|---|---|---|
| Eluent: | Pump A: Acetonitrile-Methanol (25:75) | | | |
| | Pump B: Phosphate buffer, 25 mM pH: 7.5 | | | |
| | 0.54 g KH$_2$PO$_4$ | | | |
| | 3.74 g Na$_2$HPO$_4$.2H$_2$O in 1 liter of water | | | |
| Gradient table: | Time | Pump A | Pump B | Flow |
| | Start | 30 | 70 | 1 ml/min |
| | 1 minute | 30 | 70 | 1 ml/min |
| | 26 minutes | 80 | 20 | 1 ml/min |
| | 30 minutes | 80 | 20 | 1 ml/min |
| | 32 minutes | 30 | 70 | 1 ml/min |
| | 42 minutes | 30 | 70 | 1 ml/min |
| Injection vol.: | 50 μL | | | |
| Detection: | U.V., λ: 210 nm | | | |
| Retention times: | UR-12746: 24.2 min; UR-12715: 20.1 min (approx.) | | | |

The level of azoreduction was determined from the amounts of product and UR-12715 recovered in faeces. The relative percentage of the amounts corresponding to the product (UR-12746 or sodium salt of UR-12746) and to the metabolite (UR-12715) found in faeces after oral administration are shown in Table 3. Results are given as the mean values.

TABLE 3

| | UR-12746 | | Sodium salt of UR-12746 | |
|---|---|---|---|---|
| | Product | UR-12715 | Product | UR-12715 |
| 0–24 h | 78.8% | 21.2% | 21.1% | 78.9% |
| 24–48 h | 52.5% | 47.5% | 12.1% | 87.9% |
| 0–48 h | 76.1% | 23.9% | 20.8% | 79.2% |

Similar results were obtained when the sodium salt of UR-12746 in amorphous form was used.

ii) Study in monkeys

6 Cynomolgus monkeys were used for this study. Each test product was administered to three monkeys, respectively. UR-12746 was administered as a suspension in 0.2% CMC, at a dose of 100 mg/kg p.o. (1000 mg UR-12746/10 mL of 0.2% CMC), whereas the sodium salt of UR-12746 (polymorph I) was administered as individualized capsules for each animal at a dose of 100 mg/kg p.o.

The monkeys were placed in metabolic cages, so that urine and faeces could be separately collected, and faeces corresponding to the periods 0–24 h, 24–48 h and 48–72 h were collected.

The treatment of the faeces and the determination of the amount of administered product and metabolite present in the samples were carried out following the same procedure described above for the study in rats.

As in the rat study, the azoreduction level was determined from the amounts of product and UR-12715 recovered in faeces. The results obtained are shown in Table 4:

TABLE 4

| | UR-12746 | | Sodium salt of UR-12746 | |
|---|---|---|---|---|
| | Product | UR-12715 | Product | UR-12715 |
| 0–24 h | >99% | 0% | 12.6% | 87.4% |
| 24–48 h | >99% | 0% | 6.5% | 93.5% |
| 48–72 h | >99% | 0% | 5.0% | 95.0% |
| 0–72 h | >99% | 0% | 9.7% | 90.3% |

The results of these studies clearly show that the sodium salt of UR-12746 is metabolized in the colon to a much greater extent than UR-12746. Thus, whereas just 24% of azoreduction takes place after oral administration of UR-12746 in rats, a much higher azoreduction, around 79%, is observed when the sodium salt of UR-12746 is administered. This different behaviour is still more clearly observed in monkeys, where no azoreduction is observed after administration of UR-12746 while a very high level of metabolization in the colon (around 90%) is observed when the sodium salt of UR-12746 is administered. The sodium salt of UR-12746 is therefore a more suitable compound to be used for the treatment or prevention of inflammatory bowel disease.

What is claimed is:

1. Sodium salt of
   (Z)-2-hydroxy-5-[[4-[3-[4-[(2-methyl-1H-imidazo [4,5-c]pyridin-1-yl)methyl]-1piperdinyl]-3-oxo-1-phenyl-1propenyl]phenyl ]phenyl]azo]benzoic acid of formula I:

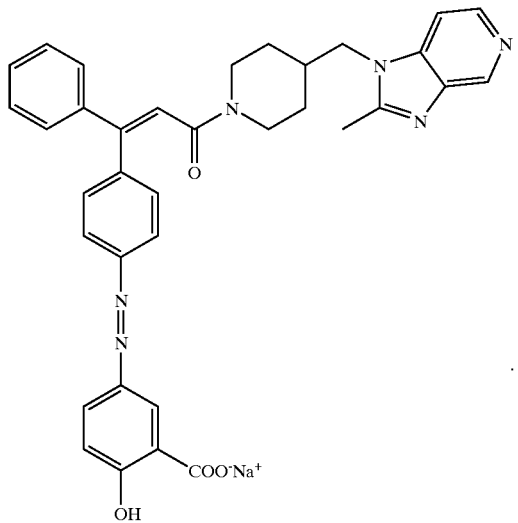

2. A compound according to claim 1, in amorphous form.
3. A compound according to claim 1, in crystalline form.
4. A compound according to claim 3, having an X-ray powder diffractogram, obtained at λ=1.542 Å and using a radiation source of Cu Kα, comprising peaks at an angle 2θ of 6.04, 6.38, 8.01, 8.54, 11.73, 13.18, 13.65, 14.55, 14.97, 16.08, 16.90, 17.23, 19.10, 19.53, 20.15, 21.12, 21.86, 22.48, 23.71, and 24.23°±0.2°.

5. A compound according to claim 3, having an X-ray powder diffractogram substantially in accordance with that shown in FIG. 5.

6. A compound according to claim 3, having an infrared spectrum substantially in accordance with that shown in FIG. 34.

7. A compound according to claim 3, having an X-ray powder diffractogram substatially in accordance with that shown in FIG. 5 and an infrared spectrum substantially in accordance with that shown in FIG. 4.

8. A compound according to claim 3, having an X-ray powder diffractogram, obtained at λ=1.542 Å and using a radiation source of Cu Kα, comprising peaks at an angle 20 of 6.07, 8.30, 8.82, 11.71, 12.52, 13.24, 15.72, 17.77, 18.96, 19.67, 20.33, 20.84, 21.39, 21.71, 22.77, 22.97, 23.50, 23.95 and 29.50°±0.2°.

9. A compound according to claim 3, having an X-ray powder diffractogram substantially in accordance with that shown in FIG. 7.

10. A compound according to claim 3, having an infrared spectrum substantially in accordance with that shown in FIG. 6.

11. A compound according to claim 3, having an X-ray powder diffractogram substantially in accordance with that shown in FIG. 7 and an infrared spectrum substantially ina accordance with that shown in FIG. 6.

12. A method of manufacturing a medicament for the treatment or prevention of inflammatory bowel disease, the method comprising incorporating an amount of the compound according to claim 1, effective to treat inflammatory bowel disease into the medicament.

13. A method of manfacturing a medicament for the treatment or prevention of inflammatory bowel disease, the method comprising incorporating an amount of the compound according to claim 2, effective to treat inflammatory bowel disease into the medicament.

14. A method of manufacturing a medicament for the treatment or prevention of inflammatory bowel disease, the method comprising incorporating an amount of the compound according to claim 3, effective to treat inflammatory bowel.

15. A process for preparing a compound according to claim 1, the process comprising treating
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid with one equivalent of sodium hydroxide in a suitable solvent.

16. A process according to claim 15, wherein the solvent is ethanol or methanol.

17. A process for preparing a compound according to claim 2, the process comprising obtaining the compound from a solution of the solution salt of
(Z)-2-hydroxy-5-[[-4-[(2-methyl-1H-imidazo[4,5-c]pyridin-1-yl)methyl]-1-piperidinyl]-3-oxo-1-phenyl-1-propenyl]phenyl]azo]benzoic acid either by evaporating the solvent or by precipitation by the addition over a second more apolar solvent.

18. A process for preparing a compound according to claim 3, the process comprising crystallization a solution of the sodium salt of
(Z)-2-hydroxy-5-[[4-[3-[4-[(2-methyl-1-H-imidazo[4,5-c]pyridin-1-yl)methyl]-1-piperdinyl]-3-oxo-1-phenyl-1-propenyl]phenyl]azo]benzoic acid in a suitable solvent of solvents.

19. A process according to claim 18, wherein the source solution of the sodium salt of
(Z)-2-hydroxy-5-[[4-[3-4-[(2methyl-1H-imidazo[4,5-c]pyridin-1yl)methyl]-1-piperidinyl]-3-oxo-1-phenyl-1-propenyl]-phenyl]azo]benzoic acid is prepared by treatment of
(Z)-2-hydroxy-5-[[4-[3-[4-](2-methyl-1H-imidazo[4,5-c]pyridin-1-yl)methyl]-1-piperidinyl]-3-oxo-1-phenyl1-propenyl]phenyl]azo]benzoic acid with one equivalent of sodium hydroxide in a suitable solvent or solvents.

20. A process according to claim 18, wherein the source solution of the sodium salt of
(Z)-2-hydroxy-5-[[4-[3-[4-[(2-methyl-1H-imidazo[4,5-c]pyridin-1yl)methyl]-1-piperidinyl]-3-oxo-1-phenyl-1-propenyl]phenyl]azo]benzoic acid is prepared from sodium salt of
(Z)-2-hydroxy-5-[[4-3-[4[(2-methyl-1H-imidazo[4,5-c]pyridin-1yl)methyl]-1-piperdinyl]-3-oxo-1-phenyl]phenyl]azo]benzoic acid previously obtained.

21. A process for preparing a compound according to claim 4, the process comprising crystallizing a solution of the sodium salt of
(Z)-2-hydroxy-5-[[4-[3-[4-[(2-methyl-1H-imidazo[4,5-c]pyridin-1-yl)methyl]-1piperidinyl]-3-oxo-1-phenyl-1-propenyl]phenyl]azo]benzoic acid in ethanol.

22. A process according to claim 21, wherein the crystallization is carried out at a temperature in the range 20–70° C.

23. A process according to claim 21, wherein the solution contains a concentration of sodium salt of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid (expressed as mL solvent/g of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid used as starting material) in the range 1.9–6.0 mL/g.

24. A process according to claim 21, wherein the solution contains less than 4% w/w of water.

25. A process according to claim 22, wherein the solution contains a concentration of sodium salt of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid (expressed as mL solvent/g of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid used as starting material) in the range 1.9–6.0 mL/g.

26. A process according to claim 22, wherein the solution contains less than 4% w/w of water.

27. A process according to claim 23, wherein the solution less than 4% w/w of the water.

28. A process according to claim 21, wherein the solution conatins less than 0.4% w/w of water, the crystallization is carried out at a temperature in the range of 20°–70° and wherein the solution contains a concentration of sodium salt of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid (expressed as mL solvent/g of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid used as starting material) in the range 1.9–6.0 mL/g.

29. A process for preparing a compound according to claim 5, the process comprising crystallizing a solution of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid in ethanol.

30. A process for preparing a compound according to claim 6, the process comprising crystallizing a solution of the sodium salt of (Z)-2-hydroxy-5-[[4-[(2-methyl-1H-imidazo[4,5-c]pyridin-1-yl)methyl]-1-piperidinyl]-3-oxo-1-phenyl-1-propenyl]azo]benzoic acid in ethanol.

31. A process for preparing a compound according to claim 7, the process comprising crystallizing a solution of the sodium salt of (Z)-2-hydroxy-5-[[4-[3-[4-[(2-methyl-1H-imidazol[4,5-c]pyridin-1-yl)methyl]-1-piperidinyl]-3-oxo-1-phenyl-1-propenyl]phenyl]azo]benzoic acid in ethanol.

32. A process for preparing a compound according to claim 8, the process comprising crystallizing a solution of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid in mixtures of ethanol or methanol with a second more apolar solvent, and optionally in the presence of a small amount of water.

33. A process according to claim 32, wherein the second more apolar solvent is ethyl acetate, acetonitrile or heptane.

34. A process according to claim 33, wherein the second more apolar solvent is ethyl acetate.

35. A process according to claim 32, wherein crystallization is carried out in a mixture of ethanol-ethyl acetate-water.

36. A process according to claim 35, wherein the crystallization is carried out at a temperature in the range between 25 and 70° C.

37. A process according to claim 35, wherein the solution contains a concentration of sodium salt of (Z)-2-hydroxy-5-[[4-[3-[4-[(2-methyl-1H-imidazo[4,5-c]pyridin-1-yl)methyl]-1-piperidinyl]-3oxo-1-phenyl-1-propenyl]phenyl]azo]benzoic acid (given as mL solvent/g starting material expressed as g of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid) of 2.8–6.6 mL ethanol/g, 5.4–15 mL ethyl acetate/g and 0.13–0.33 mL water/g.

38. A process according to claim 36, wherein the solution contains a concentration of sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid (given as mL solvent/g starting material expressed as g of
(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid) of 2.8–6.6 mL ethanol/g, 5.4–15 mL ethyl acetate/g and 0.13–0.33 mL water/g.

39. A process for preparing a compound according to claim 9, the process comprising crystallizing a solution of the sodium salt of (Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic acid in mixtures of ethanol or methanol with a second more apolar solvent, and optionally in the presence of a small amount of water.

40. A process for preparing a compound according to claim 10, the process comprising crystallizing a solution of the sodium salt of (Z)-2-hydroxy-5[[4-[3-[4-[(2-methyl-1H-imidazo [4,5-c]pyridin-1-yl)methyl]-1-piperidinyl]-3-oxo-1-phenyl-1-propenyl]phenyl]azo]benzoic acid in mixture of ethanol or methanol with a second more apolar solvent, and optionally in the presence of a small amount of water.

41. A process for preparing a compound according to claim 11, the process comprising crystallizing a solution of the sodium salt of (Z)-2-hydroxy-5-[[4-[3-[4[(2-methyl-1H-imadazo[4,5-c]pyridin-1-yl)methyl]-1-piperidinyl]-3-oxo-1-phenyl-1-propenyl]phenyl]azo]benzoic acid in mixtures of ethanol or methanol with a second more apolar solvent, and optionally in the presence of a small amount of water.

42. A pharmaceutical composition that comprises an effective amount of a sodium salt of (Z)-2-hydroxy-5[[4-[3-[4-[(2-methyl-1H-imidazo[4,5-c]pyridin-1yl)methyl-1-piperidinyl]-3-oxo-1phenyl-1-propenyl]-phenyl]azo]benzoic acid of formula I:

and one or more pharmaceutically acceptable excipients.

43. The composition of claim 42, wherein the salt is in amorphous form.

44. The composition of claim 42, wherein the salt is in crystalline form.

45. A method of treating or preventing inflammatory bowel disease, the method comprising administering an amount of a sodium salt of (Z)-2-hydroxy-5-[[4-[3-[4-[(2-methyl-1H-imidazo[4,5-c]pyridin-1-yl)methyl]-1-piperdinyl]-3-oxo-1-phenyl-1-propenyl]phenyl]azo]benzoic acid of formula I:

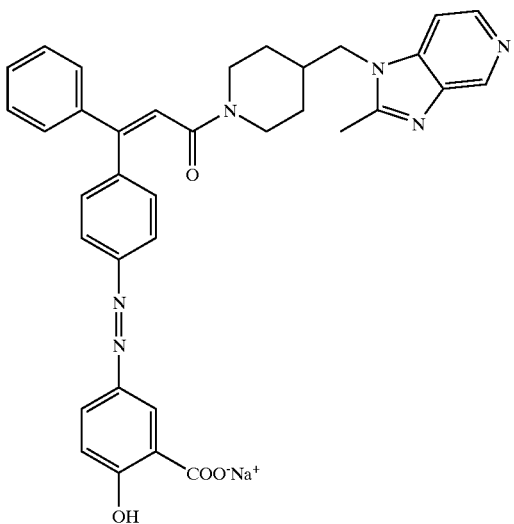

effective to treat inflammatory bowel disease to a mammal in need therof.

46. The method of claim 45, wherein the mammal is a human.

47. The method of claim 45, wherein the inflammatory bowel disease is ulcerative colitis.

48. The method of claim 45, wherein the inflammatory bowel disease is Crohn's disease.

49. The method of claim 45, wherein the salt is in amorphous form.

50. The method of claim 45, wherein the salt is in crystalline form.

51. The method of claim 49, wherein the inflammatory bowel disease is ulcerative colitis.

52. The method of claim 49, wherein the inflammatory bowel disease is Crohn's disease.

53. The method of claim 50, wherein the inflammatory bowel disease is ulcerative colitis.

54. The method of claim 50, wherein the inflammatory bowel disease is Crohn's disease.

* * * * *

UNITED STATES PATENT AND TRADEMARK OFFICE
CERTIFICATE OF CORRECTION

PATENT NO. : 6,809,087 B2
APPLICATION NO. : 10/257262
DATED : October 26, 2004
INVENTOR(S) : Elena Carceller et al.

It is certified that error appears in the above-identified patent and that said Letters Patent is hereby corrected as shown below:

<u>Column 13,</u>
Line 8, delete "34." and insert -- 4 --.
Line 66, delete "of" and insert -- or --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO. : 6,809,087 B2  Page 1 of 1
APPLICATION NO. : 10/257262
DATED : October 26, 2004
INVENTOR(S) : Elena Carceller et al.

It is certified that error appears in the above-identified patent and that said Letters Patent is hereby corrected as shown below:

Claim 8, column 13, line 15, delete ~~angle 20~~ and insert <u>angle 2θ</u>

Claim 17, column 13, line 54, delete "solution" (second occurrence) and insert --sodium--. lines 55, 56 and 57, delete ~~(Z)-2-hydroxy-5-[[-4-[(-2-methyl-1H-imidazo-[4,5-c]pyridin-1-yl)methyl]-1-piperidinyl]-3-oxo-1-phenyl-1-propenyl]phenyl]azo]benzoic~~ and insert <u>(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic</u>

Claim 20, column 14, lines 16, 17 and 18, delete ~~(Z)-2-hydroxy-5-[[4-3[4[(-2-methyl-1H-imidazo[4,5-c]pyridin-1yl)methyl]-1-piperidinyl]-3-oxo-1-phenyl]phenyl]azo]benzoic~~ and insert <u>(Z)-2-hydroxy-5-[[4-[3-[4-[(2-methyl-1H-imidazo[4,5-c]pyridin-1-yl)methyl]-1-piperidinyl]-3-oxo-1phenyl-1-propenyl]phenyl]azo]benzoic</u>

Claim 28, column 14, line 56. delete ~~conatins less than 0.4% w/w~~ and insert <u>contains less than 4% w/w</u>

Claim 30, column 15, lines 10, 11 and 12, delete ~~(Z)-2-hydroxy-5-[[4-[(2-methyl-1H-imidazo[4,5-c]pyridin-1-yl)methyl]-1-piperidinyl]-3-oxo-1-phenyl-1-propenyl]azo]benzoic~~ and insert <u>(Z)-2-hydroxy-5-[[4-[3-[4-[(2-methyl-1H-imidazo[4,5-c]pyridin-1-yl)methyl]-1-piperidinyl]-3-oxo-1-phenyl-1-propenyl]phenyl]azo]benzoic</u>

Signed and Sealed this

Twenty-eighth Day of November, 2006

JON W. DUDAS
*Director of the United States Patent and Trademark Office*